(12) United States Patent
Galvez, III et al.

(10) Patent No.: US 8,563,282 B2
(45) Date of Patent: Oct. 22, 2013

(54) MATERIALS AND METHODS FOR CONVERTING BIOMASS TO BIOFUEL

(75) Inventors: Adriano Galvez, III, Visalia, CA (US); Glenn Richards, Visalia, CA (US)

(73) Assignee: Edeniq, Inc., Visalia, CA (US)

( * ) Notice: Subject to any disclaimer, the term of this patent is extended or adjusted under 35 U.S.C. 154(b) by 765 days.

(21) Appl. No.: 12/547,830

(22) Filed: Aug. 26, 2009

(65) Prior Publication Data

US 2010/0055741 A1 Mar. 4, 2010

Related U.S. Application Data

(60) Provisional application No. 61/092,109, filed on Aug. 27, 2008.

(51) Int. Cl.
*C12P 7/06* (2006.01)

(52) U.S. Cl.
USPC .......................................................... 435/161

(58) Field of Classification Search
USPC .......... 435/101, 102, 103, 104, 105, 161, 163
See application file for complete search history.

(56) References Cited

U.S. PATENT DOCUMENTS

| 5,948,721 | A | 9/1999 | Yuansheng et al. |
| 6,043,392 | A | 3/2000 | Holtzapple et al. |
| 2007/0031953 | A1 | 2/2007 | Dunson et al. |
| 2007/0190626 | A1 | 8/2007 | Wilkening et al. |
| 2009/0000184 | A1 | 1/2009 | Garwood |
| 2010/0043782 | A1 | 2/2010 | Kilambi et al. |

FOREIGN PATENT DOCUMENTS

| WO | WO 2004/081193 A2 | 9/2004 |
| WO | WO 2005/087937 A2 | 9/2005 |

OTHER PUBLICATIONS

International Search Report and Written Opinion for PCT/US2009/055018, dated Oct. 15, 2009.
Pandey, Ashok; "Handbook of Plant-Based Biofuels"; 2009, CRC Press, 4 pages.
Naidu et al., "Effects of Ground Corn Particles Size on Ethanol Yield and Thin Stillage Soluble Solids," 2007, Cereal Chem., 84(1), pp. 6-9.
Rausch et al., "Particle Size Distributions of Ground Corn and DDGS from Dry Grind Processing," 2005, Transactions, of the ASAE, vol. 48(1); 273-277.
Supplementary European Search Report from EP 09810526.5, dated Mar. 28, 2012.
Dasari et al.; "The Effect of Particle Size on Hydrolysis Reaction Rates and Rheological Properties in Cellulosic Slurries"; *Applied Biochemistry and Biotechnology*, 136(140): 289-299 (2007).
Dickey et al.; "Foam Separation of Oil from Enzymatically Treated Wet-Milled Corn Germ Dispersions"; *J. Am. Oil Chem. Soc.*; 86:927-932 (2009).
Rausch et al.; "Particle Size Distributions of Ground Corn and DDGS from Dry Grind Processing"; *Transactions of the ASAE*; 48(1):273-277 (2005).

*Primary Examiner* — Suzanne M Noakes
*Assistant Examiner* — Stephen Chong
(74) *Attorney, Agent, or Firm* — Kilpatrick Townsend & Stockton LLP

(57) ABSTRACT

This disclosure provides for materials and methods for converting biomass to biofuels. The materials include a colloid mill with or without cellulase enzymes, and the methods include the use of a colloid mill and optionally cellulose enzymes to pretreat biomass for use in a biomass to biofuel production process.

12 Claims, 4 Drawing Sheets

MATERIALS AND METHODS FOR CONVERTING BIOMASS TO BIOFUEL

CROSS-REFERENCE TO RELATED PATENT APPLICATIONS

The present application claims benefit of priority to U.S. Provisional Patent Application No. 61/092,109, filed Aug. 27, 2008, which is incorporated by reference in its entirety.

TECHNICAL FIELD

This invention relates to the conversion of biomass to biofuels, including materials and methods for pretreatment of biomass for biofuel production process.

BACKGROUND OF THE INVENTION

The use of biomass, such as plant biomass, as a raw material for the production of biofuels such as ethanol or butanol is established as a viable alternative to carbon-based fuels. Corn is the most common biomass, with a significant number of corn ethanol plants in the United States (U.S.), but other biomass sources such as sugar beets, sugar cane, milo (sorghum), barley, corn stover, energy cane, and wood waste also are used in the U.S. and other countries.

With respect to using corn as the biomass, the kernels are made up of a variety of materials including starch, protein, oils, fiber and various organic and inorganic compounds and water. The endosperm, which contains mainly starch, typically accounts for approximately 80-85% (dry weight basis) of the corn kernel whereas the germ and the hull account for approximately 10-14% and 5-6%, respectively. The germ is high in oil, typically containing approximately 38% to 45% oil by weight.

For conversion of corn (and other starch-based biomass) to biofuel, the starch is broken down (i.e. hydrolyzed) into sugars by enzymes (also known as "liquefaction"). The resultant sugars are cooled and transferred to fermentation tanks where other enzymes, are added to break down these relatively complex sugars into simple sugars (saccharification). Yeast is also added to the fermenter where these simple sugars are used by yeast to produce ethanol or another biofuel. Once fermentation has been completed, the fermented mash is transferred through the beer well to the distillation system where solids and water are separated from ethanol through a series of fractionation stages. During fractionation, ethanol is evaporated from one stage and condensed in the next stage thereby concentrating the ethanol to approximately 95 vol %. The remainder of the water is removed by molecular sieves or membranes concentrating the ethanol to greater than 99 vol %. The bulk of the water containing the soluble and insoluble solids (known as whole stillage) are discharged from the bottom of the distillation column and then centrifuged. The majority of the suspended solids are removed as a 35% solids cake while the majority of the water with dissolved solids are split into recycled liquid (backset) or sent to an evaporator for concentration. The evaporator concentrate (~40% solids) is mixed with the cake solids and either sold in the wet state or dried in a rotary or flash dryer to a 90% solids powder know as Distillers Dry Grains with Solubles (DDGS).

BRIEF SUMMARY OF THE INVENTION

This disclosure provides materials and methods for converting biomass, such as starch-based biomass or cellulose-based biomass, to biofuel. In some embodiments, the materials include a colloid mill or other high shear milling/mixing device (hereinafter, the term "colloid mill" refers to a colloid mill itself or any other high shear/milling mixing device unless stated otherwise). In some embodiments, the colloid mills of the invention comprise a rotor and stator and optionally is capable of reducing ling fibers of biomass into smaller particles. In some embodiments, the colloid mill does not comprise spinning discs such as are described in US Patent Publication No. 2009/0000184. In some embodiments, particles within the colloid mill are not treated with steam and/or supplemental $CO_2$.

The methods of the invention include using the colloid mill to reduce and limit the overall range of the particle size of biomass, to expose more carbohydrates and/or oligosaccharides used in the biofuel production process, and to generate particle sizes of a sufficient size to allow for generation of a concentrated slurry of particles that will still be recoverable in downstream filtration (in contrast to an unpumpable matted cake of large particles and fiber, or an unrecoverable mud which forms if particle size is too small). As used herein, "particle size" can be determined by the ability of the particle to pass through a screen of a known opening diameter. The size of the particle is the smallest size screen opening that will still allow the particle to pass through. Size is roughly equivalent to the narrowest diameter of a particle, though it will be appreciated that the particles will be not necessarily be spherical and thus particle size will be most efficiently determined by measuring the ability of a particle to pass through a screen of known opening diameter. Screens generally preclude long fibers with a particular diameter as they would be trapped in the screen due to bending.

In some embodiments, the materials include a colloid mill and the method includes using the colloid mill to produce biomass particles having a relatively uniform particle size for use in a biomass to biofuel production process. In some embodiments, the materials include a colloid mill, and the method includes using the colloid mill to produce a colloidal suspension of biomass particles for use in a biomass to biofuel production process. In some embodiments, the materials include a colloid mill and a hammer mill, and the method includes using a hammer mill to produce a dry powder from the biomass for use in a biofuel production process prior to being passed through the colloid mill. In some embodiments, the materials include a colloidal mill and one or more of a hammer mill and an enzyme or cocktail of enzymes, and the method includes pretreating the biomass by using a colloid mill and one or more of a hammer mill to shear the biomass and an enzyme or cocktail of enzymes to hydrolyze the biomass. These enzymes can be added before or after the colloid mill. In embodiments in which an enzyme or cocktail of enzymes are also used in the pretreatment step, the enzymes can be cellulase or other enzymes. In some embodiments, the materials include one or more of the above-named materials, and the method includes one or more of the above-named methods. In some embodiments, the materials and methods are applied to a cellulosic feedstock in a biomass to biofuel production process. In some embodiments, the cellulosic feedstock includes corn fiber or corn stover, and the process includes producing ethanol from the corn, corn fiber and/or corn stover. In one or more of the above-mentioned embodiments, the process also comprises producing an ethanol concentration of at least 5% by volume of biofuels and up to 20% or more by volume of biofuels including alcohols, such as for example at least 13% and up to 16% or up to 20% by volume of biofuel for corn or similar biomass, or at least 4% and up to 7%, 8% or 10-12% by volume of biofuel for non-corn or cellulosic biomass.

In one or more of the above-mentioned embodiments, the process also comprises producing a yield of 2.8-3.1 gallons of ethanol per bushel of corn. In some embodiments, the process comprises the production of 60 to 80 or more gallons of ethanol per ton of biomass material.

The present invention provides methods of making biofuels. In some embodiments, the methods comprise pretreating biomass particles to reduce the particles to a relatively uniform particle size; and making biofuels from said pretreated biomass particles.

In some embodiments, said pretreating is with a high shear milling device. In some embodiments, the high shear milling device is a colloidal mill.

In some embodiments, said pretreating is performed on sheared or milled biomass.

In some embodiments, at least 85% or at least 95% of the pretreated particles have a particle size from about 100 microns to about 800 microns or about 100 microns to about 500 microns.

In some embodiments, about 100 microns to about 800 microns said biomass is corn and at least 95% of the pretreated particles have a particle size from about 100 microns to about 500 microns.

In some embodiments, the yield of said biofuels is increased compared to a method in which a colloid mill is not used to reduce the particle size of the biomass.

In some embodiments, the method further comprises contacting said biomass with at least one cellulase enzyme.

In some embodiments, the method comprises exposing biomass that has been milled with a colloid mill to at least one cellulase enzyme to produce a hydrosylate; and making biofuel from said hydrolylate. In some embodiments, said at least one cellulase enzyme is selected from the group consisting of endoglucanase, endo-1,4-beta-glucanase, carboxymethyl cellulase, endo-1,4-beta-D-glucanase, beta-1,4-glucanase, beta-1,4-endoglucan hydrolase, celludextrinase and avicelase.

In some embodiments, said exposure to said cellulase enzymes is at a temperature of about 30° C. to about 55° C. for about 24 hours to about 72 hours. In some embodiments, said exposure is to a cocktail of enzymes that convert cellulose into glucose, and hemicelluloses to xylose and arabinose. In some embodiments, said cocktail of cellulase enzymes comprises cellulases, xylanases and ligninases.

In some embodiments, the yield of said biofuels is improved compared to a method in which said milled biomass (grain, corn stover, etc. . . . ) is not exposed to at least one cellulase enzyme.

In some embodiments, the method further comprises grinding said milled biomass to a relatively uniform particle size using a colloidal mill prior to said exposure to said at least one cellulase enzyme.

In some embodiments, the making of biofuel step comprises: hydrolyzing a starch to generate sugars; and fermenting said sugars to generate said biofuels.

In some embodiments, said method of making biofuel is an industrial scale method.

In some embodiments, said fermenting is in the presence of a *S. cerevisiae* or *S. bayanus* or *P. stipitis* yeast.

In some embodiments, said biofuel is ethanol, butanol, biodiesel, or aviation fuel.

The present invention also comprises methods comprising pretreating a biomass with a colloid mill to generate biomass particles wherein at least 95% of the pretreated particles have a particle size from about 100 microns to about 800 microns.

In some embodiments, the method further comprises comminuting the biomass feedstock with a hammer mill prior to pretreating the biomass feedstock with the colloid mill.

In some embodiments, pretreated particles are used in a fermentation process.

In some embodiments, the fermentation process contains particles in a fluid mash, the colloid mill has gap rotational controls for choosing a gap size, and the downstream process further comprises separating the particles from the residual fluid mash using separation equipment, and choosing a gap size to produce particles with a relatively uniform particle size consistent for use with the separation equipment. In some embodiments, the biomass is corn, and at least 95% of the pretreated particles have a particle size of from about 150 to about 300 microns.

In some embodiments, the biomass is corn, and at least 95% of the pretreated particles have a particle size of about 150 to about 500 microns.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety.

The details of one or more non-limiting embodiments of the invention are set forth in this specification. Features, objects, and advantages of one or more possible embodiments of the invention will be apparent from the specification, and from the claims.

DETAILED DESCRIPTION OF THE INVENTION

Figure 1:
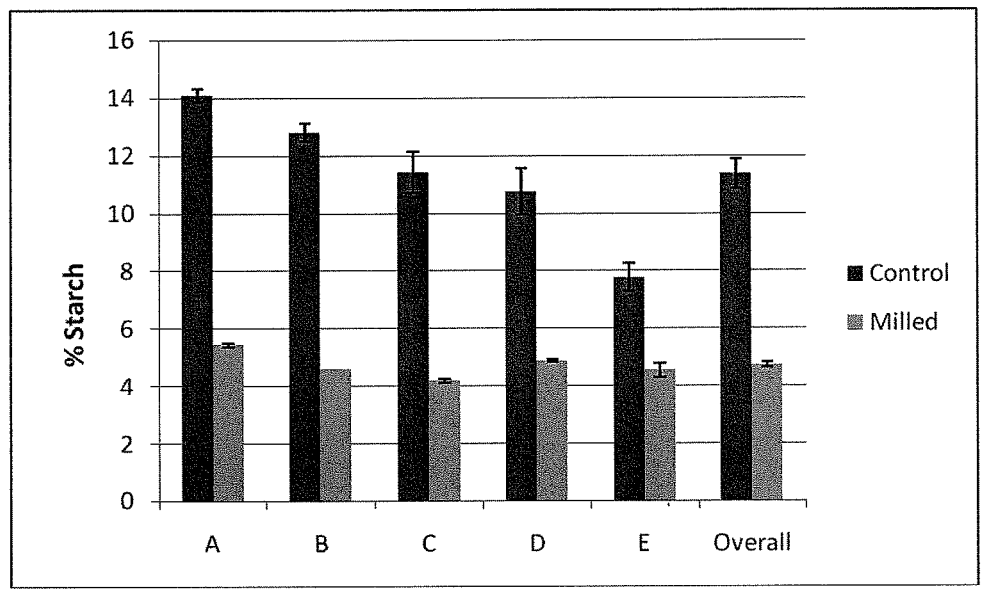
FIG. 1: DDGS residual percent starch content (dry basis) with and without colloid mill treatment.

Biomass to biofuel production can involve pretreating a biomass feedstock to produce simple sugars that are then fermented into ethanol, and recovering the ethanol product from the fermentation broth. Pretreatment can involve mechanically breaking down the biomass feedstock into smaller particles, and hydrolyzing the complex polysaccharides in the feedstock to simple sugars. Hydrolysis is performed using acids and enzymes. Fermentation can be accomplished using a cocktail of enzymes, including one or more enzymes for converting cellulose to 6-carbon sugars and then utilizing yeast to convert the sugar to ethanol or other alcohols, and one or more enzymes for converting hemicellulose to 5-carbon sugars while again utilizing yeast to convert the sugar to ethanol or other alcohols. Recovery of ethanol can involve distillation to separate the ethanol from other components of the fermentation broth, and dehydration to remove residual water from the ethanol.

This disclosure provides materials and methods for pretreating biomass in a biomass to biofuel production process. The materials and methods described herein relate to the use of a colloid mill to reduce the size of biomass in the pretreatment step of biomass to biofuels production processes.

The materials and methods described herein can be used to produce any number of biofuels. Biofuels include, without limitation, alcohols such as ethanol, methanol, propanol, and butanol, solvents such as acetone, and blends thereof. Although ethanol may be the predominant biofuel referred to in the disclosure herein, such use of 'ethanol' is not meant to limit any of the present disclosure. The colloidal mill can be used to prepare biomass for conversion to sugars that would subsequently be used to produce other biofuels including without limitation other alcohols (such as butanol) and biodiesel.

In addition to the production of biofuels, the materials and methods described herein also can be used to pretreat feedstock, for example for use in other types of applications. In some embodiments, the feedstock is pretreated for use in other fermentations such as for the production of succinic acid. The colloidal mill would prepare the feedstock for conversion to sugar that could then be utilized by an appropriate organism to produce value added by-products. For example, in some embodiments fermentations include biomass with yeast as well as *E. coli, Clostridium* and other bacteria and fungi, some of which may or may not be genetically modified. This includes production of biofuels and by-products such as succinic acid.

In some embodiments the colloid mill comminutes the municipal or industrial biomass waste prior to introducing the waste to a methane digester where bacteria are used to digest the waste first into acids and then into methane and $CO_2$ gases. In this instance the colloid mill would reduce the waste to a size that allows the waste to be more readily digested.

The materials and methods described herein can be used with virtually any biomass. Examples of biomass include, without limitation, starch crops (e.g., corn, wheat, or barley), sugar crops (e.g., sugarcane, energy cane or sugar beet), forage crops (e.g., grasses, alfalfa, or clover), and oilseed crops (e.g., soybean, sunflower, or safflower); wood products such as trees, shrubs, and wood residues (e.g., sawdust, bark or the like from forest clearings and mills); waste products such as municipal solid waste (MSW; e.g., paper, food and yard wastes, or wood), process waste and paper sludge; and aquatic plants such as algae, water weeds, water hyacinths, or reeds and rushes. Other examples of biomass include milo (sorghum), rice hulls, rice straw, wheat straw, and other straws.

Colloid mills have been used in the production of food products, paints, and cosmetics. This disclosure demonstrates, for the first time, that colloid mills can be used in the production of biofuels, specifically in the pretreatment of the biomass used in the production of biofuels. This disclosure also demonstrates, quite unexpectedly, that in some embodiments, when a colloid mill is used to pretreat biomass, mechanical preparation of the biomass may be sufficient for fermentation and an acid pretreatment step may not be required. See Example 3.

Without being bound by theory, it is believed that using a colloid mill to pretreat the biomass renders it in a form in which a suitable percentage of the starch and sugar components of the biomass are available for conversion to biofuel. It is further believed that the colloid mill renders a greater percentage of the starch and sugar components of the biomass available for conversion to biofuel than the conventional mechanical method of pretreatment using a hammer mill. This can be seen in FIG. 1 below where Trials A-E represent residual starch values in DDGS produced from fermented corn slurry with and without exposure to the colloid mill. In all trials the colloid mill-treated material resulted in more conversion of the starch thus leaving much less starch residual in the DDGS. This conversion provides value to existing facilities because less starch in the DDGS results in higher production of biofuels and increased revenue.

Figure 2:
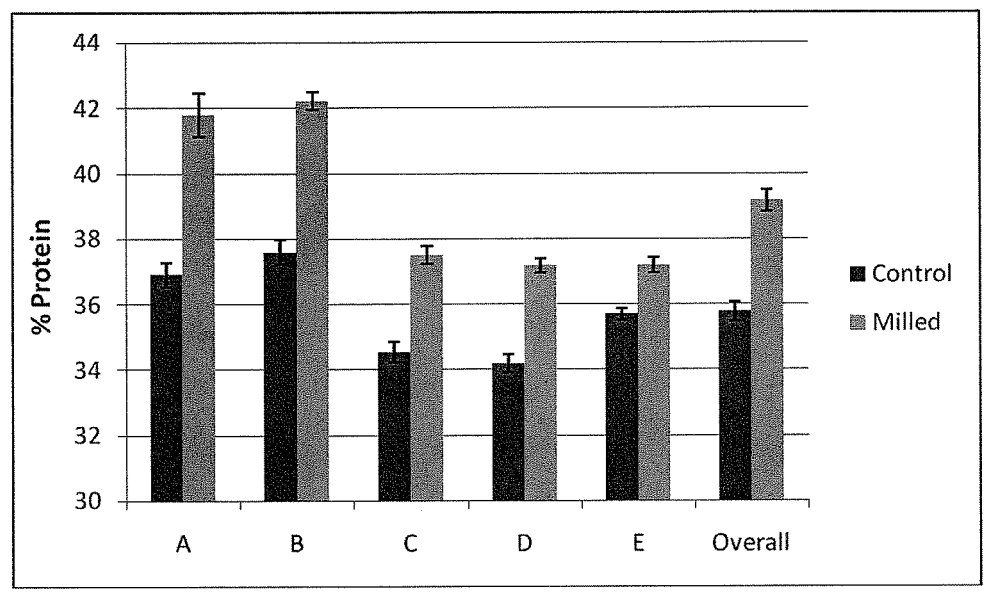
FIG. 2: DDGS protein values (dry basis) with and without colloid mill treatment.

As can be seen in FIG. 2, less residual starch in the DDGS will also result in higher protein values for the DDGS which can make the DDGS more valuable on a per ton basis.

For example, compared to the hammer mill, which comminutes biomass into random, relatively large and non-uniform sizes, the colloid mill can convert the raw biomass feedstock, when mixed with a liquid such as water, into a slurry with relatively uniform, and small particle sizes. Accordingly, the present invention provides for the use of a colloid or other high sheer mill to generate a uniform population of pretreated biomass particles that are pumpable, that is that can be pumped as a slurry. Generally, as the amount of biomass increases per volume of liquid, biomass particles will no longer be pumpable and instead will form a matted cake mass (as opposed to a slurry).

| BioMass | Pumpable solids prior to colloid mill | Pumpable solids after colloid mill | % weight of processed material <0.5 mm in size |
|---|---|---|---|
| Corn stover | 12% BDS | 21% BDS | 90 |
| Orchard waste | 13% BDS | 26% BDS | 96 |
| Switch grass | 12% BDS | 21% BDS | 90 |
| Corn kernals | 38% BDS | 46% BDS | 98 |

*BDS = bone dry solids

As shown in the table above, pre-treatment of biomass with a colloid mill renders particle size of a sufficient size to allow for a much higher concentration of pumpable solids in a slurry compared to particles generated by a hammer mill alone. For example, whereas the solids pretreated with a hammer mill only ranged from 12-38% BDS, the solids further treated with a colloid mill ranged from 21-46% BDS. Without intending to limit the scope of the invention, it is believed that the colloid mill reduces the size of larger particles (e.g., between 800-1500 microns) while not reducing the size of smaller particles (e.g., 100-500 microns). Thus, the colloid mill generates a more uniformly sized population of particles. Moreover, the particle size in this population is sufficiently large so as to allow for a recoverable high concentration slurry. Thus, in some embodiments, the biomass particle size, following colloid mill pre-treatment, is sufficient to generate a pumpable slurry comprising at least 15%, 17%, 19%, 21%, 23%, or 25% BDS from cellulosic biomass (including but not limited to stems, woody material or harvest plant waste). In some embodiments, the biomass particle size, following colloid mill pre-treatment, is sufficient to generate a pumpable slurry comprising at least 40, 42, or 44%% BDS from feedstock biomass (including but not limited to grains, such as corn kernals).

For purposes of this specification, "relatively uniform size" means that on average the particles are more similar in size than particles produced when biomass is pretreated using a hammer mill or similar grinding device such as a pin mill or roller mill. A typical hammer mill used for grinding whole corn kernels has a particle size mostly ranging from 100 to 1600 microns, distributed by weight in a bell shaped curve within that region.

In some embodiments, a corn or other biomass powder generated by a hammer mill is mixed with fresh water and backset, to make for example a 30% solids mash that can be passed through a colloidal mill. The gap setting in the mill controls maximum particle size. The fluid pumped into the milling head chamber can be at ambient temperature or heated, sometimes in the range of 90° C. to 100° C. Passing through the colloidal mill, particles from the hammer mill, e.g., of 100 to 1600 microns, can be typically processed to a range of 100 to 500, or 100 to 800 microns, for example in the 100 to 500 micron range with at least 85% or 95% by weight of the total particles having a particle size of less than 800 microns.

A colloid mill can be used to produce particles down to 1 micron in size and although this can result in a more favorable yield of converting a given weight of biomass to biofuels, the limiting factor becomes the ability of the downstream separation equipment to handle these small particles with a reasonable recovery rate. Currently, separation equipment is not well suited for handling very small particles (<10 microns). Preference therefore is not to attain the smallest possible sizes because very small particles are difficult to separate from the fluid mash. If the particle size distribution is controlled in a narrow range, the particles are more easily separated by existing centrifuges within the ethanol production plant. However, the colloid mill can be used to prepare such small particle sizes, and if separation equipment changes and can accommodate or works more efficiently with smaller particle sizes, the colloid mill can be used to create those smaller size particles by modifying the gap setting.

In some embodiments, a colloid mill is used as the only pretreatment step in a biomass to biofuel production process. In some embodiments, a colloid mill is used to pretreat biomass in a biomass to biofuel production process together with at least one other method of pretreatment. In some embodiments the further pretreatment processes include one or more of comminuting the biomass using a hammer mill and hydrolyzing the biomass using an enzyme or cocktail of enzymes. See Examples 2 and 3. In some embodiments, in which pretreatment includes the use of one or more enzymes to hydrolyze the biomass, the enzymes can be chosen from alpha amylase, beta amylase, gluconase, cellulase, beta-glucosidase, xylanase, ligninase, peroxidase, magnesium peroxidase, and endoglucanase or mixtures thereof.

In some embodiments, the biomass feedstock is corn, corn stover or corn silage and the biofuel produced is ethanol. In other embodiments the feedstocks may include a wide range of agricultural materials as mentioned above and the final biofuel could be ethanol or other alcohols such as butanol, biodiesel and also aviation fuel via fermentation of sugars. In some embodiments, pretreating biomass in a biomass to biofuel production using a colloid mill results in an increase in the yield of biofuel as compared to a similar biomass to biofuel production process using only a hammer mill. In some embodiments, colloid mill pretreatment results in a yield increase of 0.25 to 2.5 or 2.5 to 10% more gallons of biofuel per ton of biomass based on the initial particle size commonly achieved in hammer mills and the gap setting on the colloidal mill.

Without being bound by theory, it is believed that the tradeoffs as previously mentioned are that as the particle size progressively gets smaller through shearing, yields increase through exposure of sugars, starches and cellulose to the fermentation media containing yeasts and enzymes and conversely, those particles become increasingly more difficult to separate as they continue to get smaller during the fermentation process. Commercial colloid mills have a gap setting that can be dynamically adjusted to accommodate subtle differences in each biofuel plant including the percent backset, type of centrifuge or other particle separation process equipment, and other factors. In some embodiments, one or more methods described herein, may be used in combination to increase the final yield of biofuel above the yield achieved by any one of the methods independently. In some embodiments, methods described herein may improve and optimize the separation of corn oil from the spent distillation liquid (known as stillage).

Colloid Mills and Their Use in Biofuels Production

Colloid mills are available in various sizes and materials of construction. A person skilled in the art would be able to optimize the size and metallurgy for various biomass. For example two IKA model MK2000/50 can be utilized in duplex stainless steel for a 50MMGPY (million gallons per year) corn fermentation process while a single IKA model MK2000/50 comprised of 304 stainless steel parts is all that is required for a 30MMGPY sugar cane cellulosic process. In each instance, gap size is optimized for the various feedstock material input as well as various flow rate conditions.

As shown in Examples 2 and 3 below, a colloid mill can be used to pretreat biomass, such as corn biomass. In some embodiments, such as those shown in the Examples, pretreatment with a colloid mill can improve the yield of ethanol production when compared to pretreatment with a hammer mill alone. The colloid mill can be retrofitted, for example in current corn ethanol production plant by being inserted in-line between a mix tank and a liquefaction tank. The colloid mill can also be used in designing and building new biofuels production plants.

The colloidal mill can be used to select the resulting particle size distribution through the use of gap rotational controls. A relatively precise particle size distribution can be obtained from much larger biomass material using a colloid mill in contrast to alternative pretreatment techniques such as comminution with a hammer mill. An appropriate gap size on the colloid mill can produce a highly uniform suspension of biomass, where the maximum particle size of the biomass is greatly reduced and significantly more uniform compared to using only the comminution device. The radial gap size for a colloidal mill used in a corn ethanol plant can range from 0.104-0.728 millimeters, e.g., from 0.104-0.520 millimeters, e.g., from 0.208-0.520 millimeters, such that the resulting particle sizes are in the range of 100-800 microns. For example, in some embodiments, a gap setting of 0.1-0.15 is used for corn stover or other cellulosic biomass and a gap setting of 0.2-0.3 mm is used for grains including but not limited to corn kernels. As shown in FIG. 1 below, the use of a colloid mill to produce relatively precise, uniform particles sizes with high surface area results in a greater percent of starch, cellulose and sugar being available for enzymatic conversion than a hammer mill, leading to improved yield.

Typically, as discussed earlier, the finer the biomass the better the attained yield with respect to gallons of biofuel per ton of biomass. However, a serious overriding factor in the overall process is the recovery of residual solids after the biofuel has been removed. This factor as explained above results in an optimal biomass size of 100-500 microns for corn ethanol. For cellulosic processes that utilize rice straw, sugar cane, energy cane and other materials (such as those listed on page 4 above) where state of the art filtration equipment can be installed, biomass size can be from 50-350 microns, typically from 75-150 microns.

Colloid mills may also have one or more of the following additional features when used in combination with biomass pretreatment. Colloid mills can tolerate fibers of various lengths and rapidly convert them to a very controlled particle size while shearing the material and releasing or exposing more carbohydrate and/or cellulose material to enzymatic degradation. The colloid mill also optionally removes the need for facilities to operate a jet cooker. The jet cooker uses high pressure steam to assist in the release of starch from the biomass and is not required when using a colloid mill in the process. This would result in 35,000 MMBTU/year in energy savings for a 50 million gallon per year biofuel plant. With natural gas costs at $5.00/MMBTU the facility would save $176,000/year.

Commercially available colloid mills may process material at rates of 350 gallons per minute (gpm) up to and exceeding 500 gpm. This allows for a commercially viable number (3-4) of mills to be used in processes that make above 100MMGPY of biofuels. Colloid mills also may allow for more efficient centrifugal separation of solids following the fermentation process because of the uniform particle size they produce.

The weight range of solids in the corn mash in most biofuels plants is 25-35 wt % (db). A colloidal mill placed in-line between a mix tank and a liquefaction tank can tolerate the entire range of solids typically encountered and, due to the high uniformity of particle size and lower fluid viscosities achieved, also allows for higher loadings of biomass (e.g., in the range of 40 wt %) than a similar process in the absence of a colloid mill.

In some instances, biomass can be introduced directly into a colloid mill. In other instances, however, the biomass undergoes one or more pretreatment steps prior to being introduced into the colloid mill. For example, the biomass can be pretreated first with a communition device (e.g., a hammer mill, macerator), which generally breaks apart the biomass and results in a large and random distribution of particle sizes, which is later followed by a more precise grinding using a colloidal mill or a macerator followed by a colloid mill, which results in relatively uniform particles of a desired size. For example, biomass from different materials, such as but not limited to, corn and rice straw can be fed through a hammer mill with a fixed set of sieve sizes such as #7 or #8. The hammer mill can then be coupled to a colloidal mill with an adjustable gap setting for dynamically dialing in the desired particle size of the biomass.

The temperature and pH at which a colloid mill can be utilized for corn ethanol typically is that temperature and pH at which the particular amylase enzyme used in the facility is functional. For example, in a conventional corn ethanol operation, a colloidal mill can be operated at a pH in the range of about 3.8 to about 6.2 (e.g., about 4.2 to about 5.5, or about 4.5 to about 5.0) and a temperature from about 30° C. to about 120° C. Exemplary temperatures are in the range of about 76° C. to about 84° C., or, for high temperature enzymes such as Fuelzyme®, a colloid mill can be operated at a temperature that is in the range of about 85° C. to 96° C. Similarly, the temperature and pH at which the colloid mill would be utilized in connection with pretreating other biomass, would be the temperature and pH at which the enzymes used in the particular facility are functional.

Cellulase Treatment

In conventional biofuels operations, a significant amount of starch is lost for ethanol production and discarded in the form of by-products such as Distiller's Dried Grains with Solubles (DDGS). DDGS typically contains about 12-15% cellulose and hemicellulose by weight on a dry weight basis (db), to which about 4-10% by weight starch (db) can be bound. This disclosure describes the use of cellulase enzymes to free-up and recover additional glucose, xylose and arabinose usually lost or discarded in conventional practices. The present disclosure demonstrates that the use of cellulase enzymes increases and improves the yield of ethanol over existing conventional processes that do not use cellulase enzymes. This breakdown of cellulose and hemi-cellulose also results in the release of starch that was previously bound with the cellulose and hemi-cellulose. Biomass can be hydrolyzed using cellulase enzymes at temperatures from about 50° C. to 55° C. for about 2 hours up to 24 hours at a pH of 4.0-4.5. Biomass can be exposed to cellulase enzymes at any number of stages throughout the process of making biofuels from biomass. For example, biomass can be exposed to one or more cellulase enzymes after it has been processed through a cumminution device. Results herein suggest that the use of a colloidal mill, for example to produce a colloidal suspension of biomass, allows for the cellulase enzymes to better access and hydrolyze the cellulose and hemi-cellulose in the biomass. Therefore, although not required, the overall yield can be improved by exposing the biomass to one or more cellulase enzyme after the biomass has been processed through a colloid mill, or through both a comminution device and a colloid mill as described herein. Additionally or alternatively, biomass can be exposed to one or more cellulase enzyme during and/or following exposure of the biomass to the gluco-amylase enzymes (e.g., during or following saccharification).

In accordance with the present invention, there may be employed conventional molecular biology, microbiology, and biochemical techniques within the skill of the art. Such techniques are explained fully in the literature. The invention will be further described in the following examples, which do not limit the scope of the invention described in the claims. The methods and materials described herein can be incorporated into existing biofuels operations, or the methods and materials described herein can be included in designing new biofuels operations.

EXAMPLES

Example 1

Conventional Biofuels Production Using a Hammer Mill as Compared to Hammer Mill Plus a Colloid Mill Corn kernels were comminuted into corn flour using a traditional hammer mill with a #7 sieve or screen. The particle size distribution ranged from less than 50 microns up to 1400 microns. The distribution curve was bell shaped, meaning that the resulting flour contained a significant portion of large particles. The resulting flour was mixed with backset from the plant water system, which is predominantly water and residual particles, at about 32 wt % (db). A high temperature-tolerant amylase (Fuelzyme® (Verenium, Cambridge, Mass.)) then was added to the blend of corn flour, water and backset, and the mixture was heated at 87.8° C. for 2 hours at a pH of 5.0.

Figure 3:
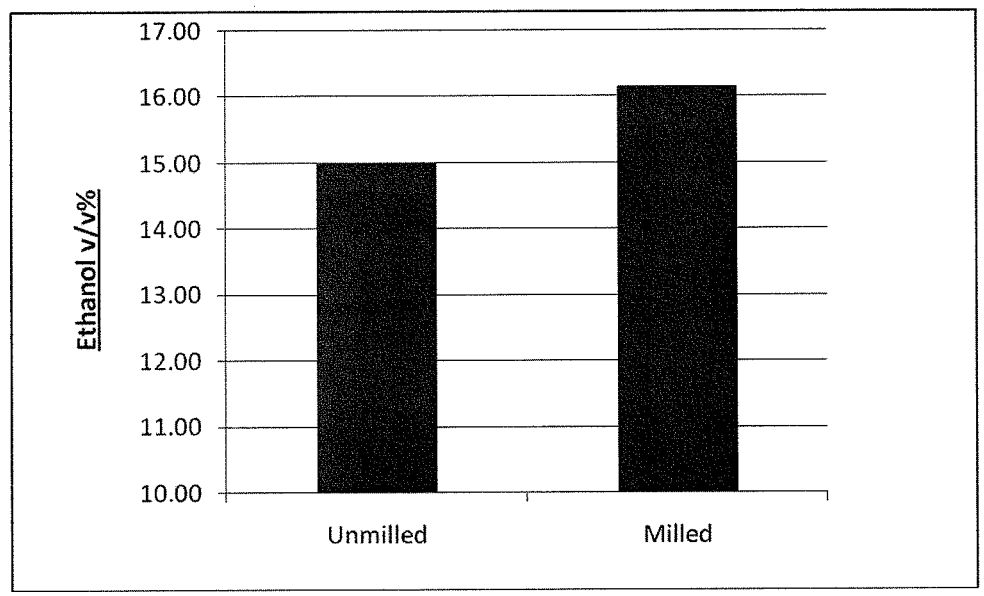
FIG. 3: Percent ethanol production of milled and unmilled biomass. This data represents a 1.17% v/v boost in ethanol, or nearly an 8% yield increase, when using the colloid mill on corn for ethanol production.
Figure 4:
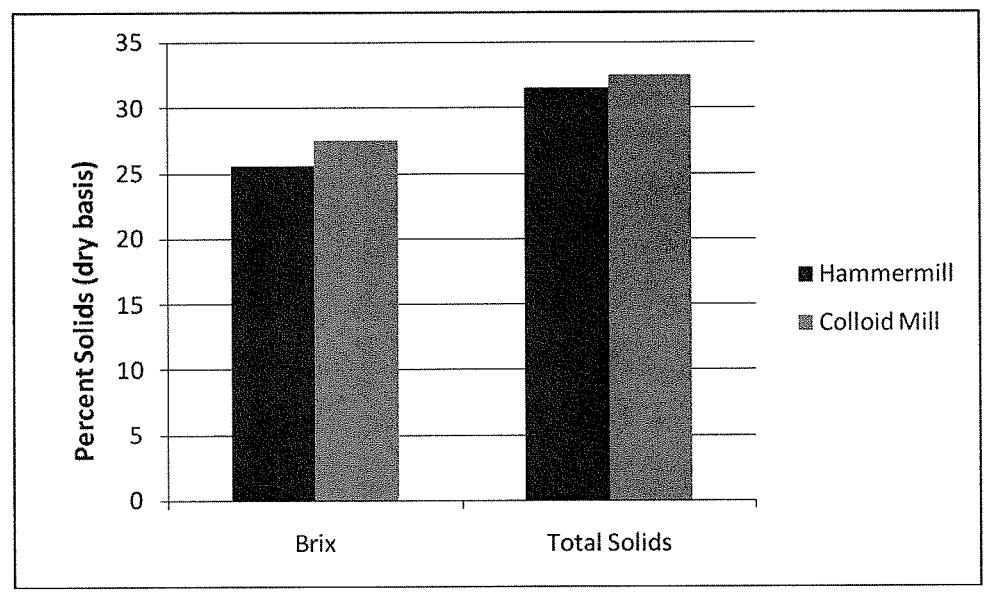
FIG. 4: This data compares the dissolved solids (Brix) and total solids (on a dry weight basis) for a liquid slurry made from a hammermill and from the same slurry then passed through a colloid mill.
Figure 5:
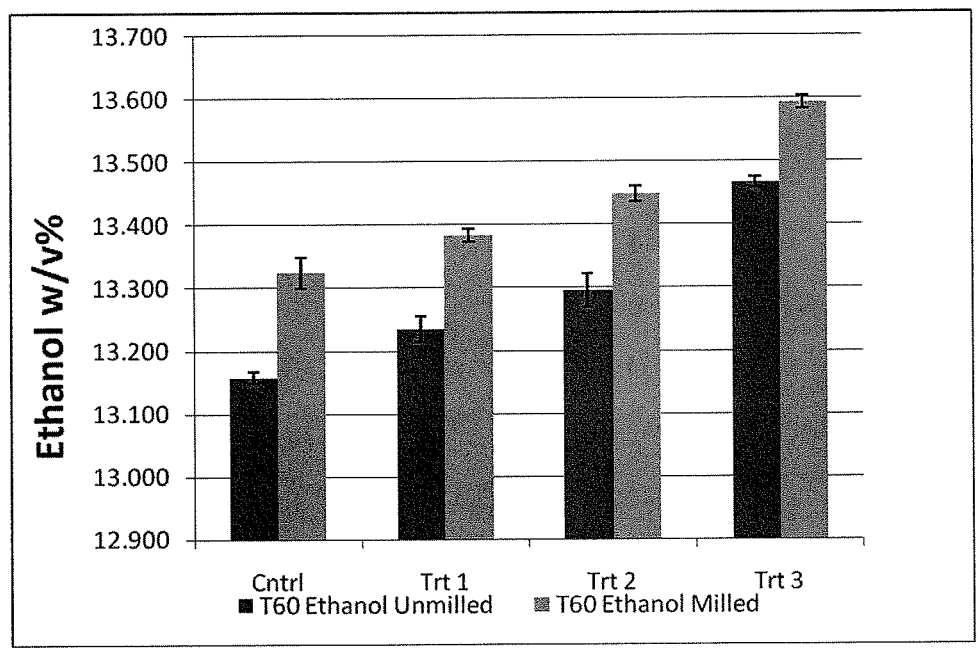
FIG. 5: Hammer and colloid mill treatment of corn with and without cellulases.
Figure 6:
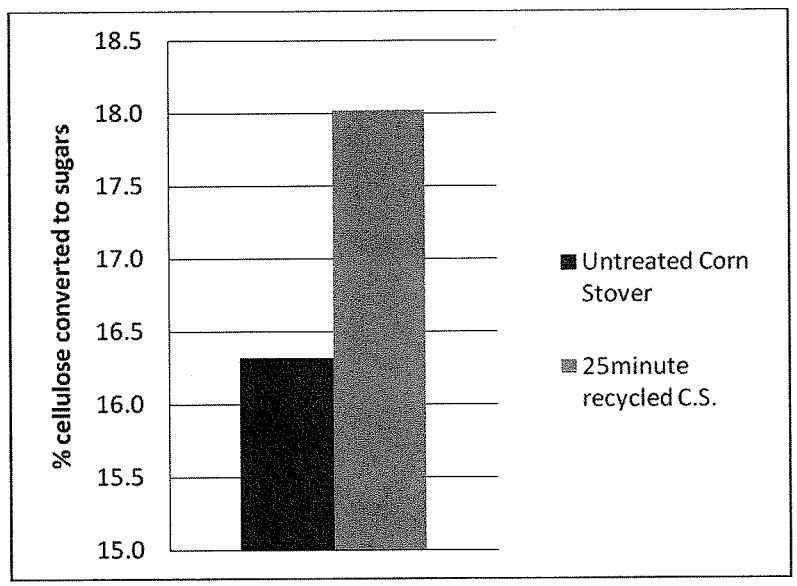
FIG. 6: Comparison of corn stover with and without treatment by the colloid mill.
Figure 7:
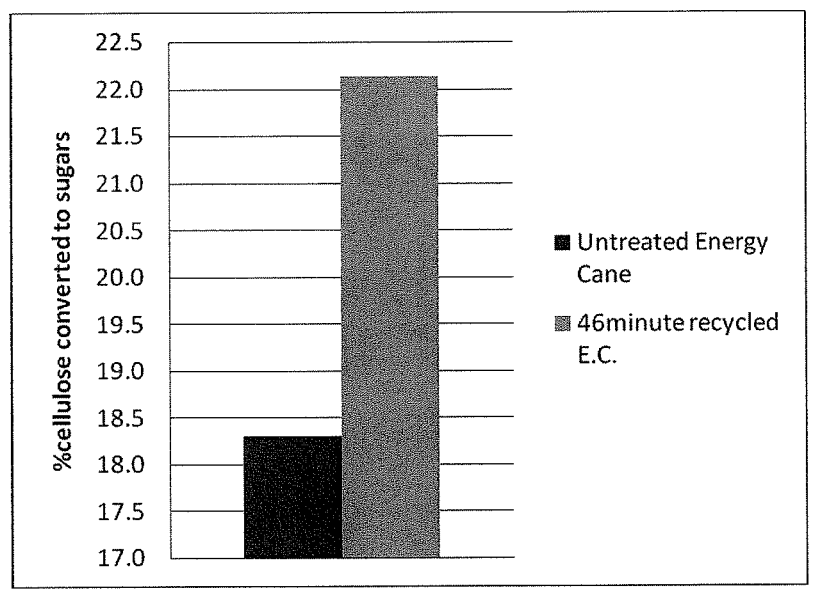
FIG. 7: Comparison of energy cane hydrolysis values with and without treatment by the colloid mill.

Following the initial liquefaction, the corn mash was cooled to 35° C. and additional enzymes (glucoamylases) were added to further continue the saccharification process and begin converting cellulose into sugars, primarily glucose. Yeast was added to the mash along with urea to provide a nitrogen source. The yeast used was a commercially available yeast similar to those produced by North American Bioproducts Corp. (NABC), Atlanta, Ga. and Fermentis, Marcq-en-Baroeul, France. The liquid mash was fermented in the presence of the yeast for 72 hours to complete the conversion of glucose sugars into ethanol. This procedure resulted in a concentration of ethanol of about ~15.0 vol % for material only subjected to the hammer mill and ~16.2 v % for corn subjected to hammer mill plus colloid mill (FIG. 3). This data represents a ~1.17% v/v boost in ethanol concentration and nearly an 8% boost in ethanol yield (gal/bu) when using the colloid mill on corn for ethanol production.

Example 2

Conventional Biofuels Production Using a Hammer Mill Compared to a Colloid Mill with and without the Inclusion of Cellulases Corn kernels were comminuted into corn flour using a traditional hammer mill with a #7 sieve or screen. The particle size distribution ranged from less than 50 microns up to 1400 microns. The distribution curve was bell shaped, meaning that the resulting flour contained a significant portion of large particles. The resulting flour was mixed with backset from the plant water system, which is predominantly water and residual particles, at about 32 wt % (db). A high temperature-tolerant amylase (Fuelzyme® (Verenium, Cambridge, Mass.)) then was added to the blend of corn flour, water and backset, and the mixture was heated at 87.8° C. for 2 hours at a pH of 5.0.

Following the initial saccharification, the corn mash was cooled to 35° C. and additional enzymes (glucoamylases) were added to further continue the saccharification process and begin converting cellulose into sugars, primarily glucose. Yeast was added to the mash along with urea to provide a nitrogen source. A commercially available yeast similar to those produced by North American Bioproducts Corp. (NABC), Atlanta, Ga. and Fermentis, Marcq-en-Baroeul, France was used. The liquid mash was fermented in the presence of the yeast for about 60 hours to complete the conversion of glucose sugars into ethanol. Treatment 1 (Trt 1) is 1.5% (w/w) cellulase by cellulose and 0.1% hemicellulase by solids; Treatment 2 (Trt 2) is 3% cellulase by cellulose and 0.25% hemicellulase by solids and Treatment 3 (Trt 3) is 15% cellulase by cellulose and 0.5% hemicellulase by solids.

This example shows that the addition of cellulases improves the amount of ethanol w/v % in combination with the colloid mill and treated by cellulases. For example, when cellulases are added to colloid material (at a gap setting of 0.2-0.3), the total ethanol production increased over corn treated with a hammer mill only was 0.225 w/v % compared to an increase of only 0.1665 w/v % without the addition of cellulases. Colloid mill treatment made smaller particle sizes that allow for the cellulases to convert sugars into glucose.

Example 3

Improved Conversion of Sugars from Corn Stover After Treatment with the Colloid Mill Corn stover material was ground to a powder by a hammermill. This material was then rehydrated to achieve a 10% dry solids weight of corn stover. Material was run through the colloid mill on a 25 minute continuous loop at a gap setting of 0.1-0.15 mm. After being treated by the colloid mill, the material was incubated at 50° C. with a cellulase and hemicellulase. At 24 hours, the material that was recirculated through the colloid mill had ~10% more sugars released from the saccharification process as compared to the material that was untreated.

Example 4

Improved Conversion of Glucose from Energy Cane After Treatment with the Colloid Mill Energy cane material was ground to a powder. This material was then rehydrated to achieve a 10% dry solids weight. Material was run through the colloid mill on a 5 minute loop. After being treated by the colloid mill, the material was incubated at 50° C. with a cellulase and hemi-cellulase. At 24 hours, the material that was recirculated through the colloid mill had >17% more sugar released from the saccharification process as compared to the material that was untreated.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of generating sugar from biomass, the method comprising,
a) providing a biomass/water mixture;
b) pretreating the biomass/water mixture with a colloid mill, wherein the colloid mill has a radial gap setting between 0.104 and 0.728 millimeters, thereby reducing the size of biomass particles in the biomass/water mixture and rendering a greater percentage of starch and sugar components of the biomass available compared to pretreatment of the biomass with a hammer mill alone; and
c) contacting the pre-treated biomass/water mixture with enzymes.

2. The method of claim 1, wherein the enzymes convert components of the biomass to sugar.

3. The method of claim 1, wherein the enzymes are selected from a gluconase, a cellulase, a beta-glucosidase, a xylanase, a ligninase, a peroxidase, a magnesium peroxidase, an endo-glucanase and a mixture thereof.

4. The method of claim 1, wherein the enzymes are selected from an alpha amylase and a beta amylase.

5. The method of claim 1, further comprising fermenting the sugars, thereby producing ethanol.

6. The method of claim 1, comprising separating particles from the biomass/water mixture after the contacting.

7. The method of claim 4, wherein 60-80 gallons of ethanol are produced per ton of biomass.

8. The method of claim 1, wherein the pretreating generates a pumpable slurry of particles recoverable in downstream filtration.

9. The method of claim 8, further comprising pumping the slurry to a different location; and
   filtering the slurry, thereby separating the particles from liquid in the slurry.

10. The method of claim 8, wherein the biomass is grain and the slurry comprises at least 40% bone dry solids (BDS).

11. The method of claim 8, wherein the biomass is cellulosic biomass and the slurry comprises at least 15% bone dry solids (BDS).

12. The method of claim 8, wherein the slurry comprises 21-46% bone dry solids (BDS).

* * * * *